US009591268B2

(12) United States Patent
Stoops et al.

(10) Patent No.: US 9,591,268 B2
(45) Date of Patent: Mar. 7, 2017

(54) FLOW CELL ALIGNMENT METHODS AND SYSTEMS

(71) Applicant: INTELLIGENT BIO-SYSTEMS, INC., Waltham, MA (US)

(72) Inventors: David Ray Stoops, Wayland, MA (US); Phillip Alan Veatch, Arlington, MA (US); Steven Jeffrey Gordon, Weston, MA (US)

(73) Assignee: QIAGEN Waltham, Inc., Waltham, MA (US)

( * ) Notice: Subject to any disclaimer, the term of this patent is extended or adjusted under 35 U.S.C. 154(b) by 429 days.

(21) Appl. No.: 13/832,509

(22) Filed: Mar. 15, 2013

(65) Prior Publication Data

US 2014/0267669 A1    Sep. 18, 2014

(51) Int. Cl.
*C12Q 1/68*    (2006.01)
*G01N 21/64*    (2006.01)
(Continued)

(52) U.S. Cl.
CPC ............... *H04N 7/18* (2013.01); *G01N 15/14* (2013.01); *G06T 7/0012* (2013.01);
(Continued)

(58) Field of Classification Search
CPC . G06T 2207/30072; G06T 2207/10056; G06T 2207/30024; C12Q 1/6869;
(Continued)

(56) References Cited

U.S. PATENT DOCUMENTS 5,374,395 A    12/1994    Robinson
5,502,773 A    3/1996    Tibbetts
(Continued)

FOREIGN PATENT DOCUMENTS

EP    1507217    2/2005
WO    0027521    5/2000
(Continued)

OTHER PUBLICATIONS

International Search Report and Written Opinion of PCT International Application No. PCT/US2014/23490 dated Jun. 17, 2014.
(Continued)

*Primary Examiner* — Dave Czekaj
*Assistant Examiner* — Alison Slater
(74) *Attorney, Agent, or Firm* — RatnerPrestia (57) ABSTRACT

Imagers and alignment methods for use by imagers imaging deoxyribonucleic acid (DNA) fragments on a flow cell are disclosed. The imagers capture intensity values at DNA fragment bead locations in tiles with each tile having a reference location in the flow cell. Flow cells may be aligned by obtaining a dark field image of each tile during a first imaging session, identifying dark field constellations of bead locations within two separate tiles during the first imaging session, identifying corresponding constellations during a second imaging session, altering the reference location of at least one tile during the second imaging session to correct for a linear offset in the corresponding constellations, and applying at least one correction factor for reading out intensity values from the imager for the bead locations in the flow cell to correct for an angular offset determined from offsets in the corresponding constellations.

29 Claims, 6 Drawing Sheets

(51) Int. Cl.
  *H04N 7/18* (2006.01)
  *G01N 15/14* (2006.01)
  *G06T 7/00* (2006.01)
  *G01N 15/00* (2006.01)

(52) U.S. Cl.
  CPC .... *G06T 7/0042* (2013.01); *G01N 2015/0038* (2013.01); *G01N 2015/144* (2013.01); *G06T 2200/32* (2013.01); *G06T 2207/10056* (2013.01); *G06T 2207/30024* (2013.01)

(58) Field of Classification Search
  CPC ..... C12Q 1/6806; C12Q 1/6825; G06F 19/20; B01L 3/502715; B01L 2200/0668; B01L 2300/0877; G01N 27/44726; G01N 27/44791; G01N 2021/6419; G01N 2021/6421; G01N 21/6428; G01N 15/14; G01N 2015/144; G01N 21/6486
  USPC .............................................. 348/79; 382/128
  See application file for complete search history.

(56) References Cited

U.S. PATENT DOCUMENTS

| | | |
|---|---|---|
| 5,695,934 A | 12/1997 | Brenner |
| 5,720,923 A | 2/1998 | Haff |
| 5,756,334 A | 5/1998 | Perler |
| 5,863,722 A | 1/1999 | Brenner |
| 5,900,481 A | 5/1999 | Lough |
| 5,981,956 A | 11/1999 | Stern |
| 6,136,543 A | 10/2000 | Anazawa |
| 6,207,960 B1 | 3/2001 | Stern |
| 6,223,128 B1 | 4/2001 | Allex |
| 6,242,193 B1 | 6/2001 | Anazawa |
| 6,255,475 B1 | 7/2001 | Kwiatkowski |
| 6,309,836 B1 | 10/2001 | Kwiatkowski |
| 6,337,188 B1 | 1/2002 | Head |
| 6,404,907 B1 | 6/2002 | Gilchrist |
| 6,448,066 B1 | 9/2002 | Wheatcroft |
| 6,576,424 B2 | 6/2003 | Fodor |
| 6,596,483 B1 | 7/2003 | Choong |
| 6,597,000 B2 | 7/2003 | Stern |
| 6,611,767 B1 | 8/2003 | Fiekowsky |
| 6,613,513 B1 | 9/2003 | Parce |
| 6,639,088 B2 | 10/2003 | Kwiatkowski |
| 6,646,243 B2 | 11/2003 | Pirrung |
| 6,664,079 B2 | 12/2003 | Ju |
| 6,756,207 B1 * | 6/2004 | Giuliano ............... B82Y 5/00 435/287.8 |
| 6,867,851 B2 | 3/2005 | Blumenfeld |
| 6,890,741 B2 | 5/2005 | Fan |
| 6,929,944 B2 | 8/2005 | Matson |
| 7,033,754 B2 | 4/2006 | Chee |
| 7,037,687 B2 | 5/2006 | Williams |
| 7,052,847 B2 | 5/2006 | Korlach |
| 7,057,026 B2 | 6/2006 | Barnes |
| 7,085,651 B2 | 8/2006 | Yasuda |
| 7,110,618 B2 | 9/2006 | Bobrov et al. |
| 7,145,645 B2 | 12/2006 | Blumenfeld |
| 7,157,228 B2 | 1/2007 | Hashmi |
| 7,169,560 B2 | 1/2007 | Lapidus |
| 7,200,254 B2 | 4/2007 | Kira |
| 7,233,393 B2 | 6/2007 | Tomaney |
| 7,270,951 B1 | 9/2007 | Stemple |
| 7,279,563 B2 | 10/2007 | Kwiatkowski |
| 7,282,337 B1 | 10/2007 | Harris |
| 7,306,918 B2 | 12/2007 | Hashmi |
| 7,315,637 B2 * | 1/2008 | Xi et al. .............. 382/128 |
| 7,329,496 B2 | 2/2008 | Dower |
| 7,344,865 B2 | 3/2008 | Parce |
| 7,386,399 B1 | 6/2008 | Izmailov |
| 7,387,891 B2 | 6/2008 | Boege |
| 7,405,823 B2 | 7/2008 | Tomaney |
| 7,414,116 B2 | 8/2008 | Milton |
| 7,425,416 B2 | 9/2008 | Hashmi |
| 7,427,673 B2 | 9/2008 | Balasubramanian |
| 7,476,504 B2 | 1/2009 | Turner |
| 7,482,120 B2 | 1/2009 | Buzby |
| 7,482,167 B2 * | 1/2009 | Sammak et al. ............... 436/164 |
| 7,491,498 B2 | 2/2009 | Lapidus |
| 7,508,516 B2 | 3/2009 | Sugiyama |
| 7,541,444 B2 | 6/2009 | Milton |
| 7,544,794 B1 | 6/2009 | Benner |
| 7,566,537 B2 | 7/2009 | Balasubramanian |
| 7,566,538 B2 | 7/2009 | Parce |
| 7,567,695 B2 | 7/2009 | Frost |
| 7,592,435 B2 | 9/2009 | Milton |
| 7,635,562 B2 | 12/2009 | Harris |
| 7,635,565 B2 | 12/2009 | Hashmi |
| 7,635,578 B2 | 12/2009 | Ju |
| 7,635,588 B2 | 12/2009 | King |
| 7,666,593 B2 | 2/2010 | Lapidus |
| 7,680,790 B2 | 3/2010 | Indeck |
| 7,687,260 B2 | 3/2010 | Gutekunst |
| 7,713,698 B2 | 5/2010 | Ju |
| 7,714,303 B2 | 5/2010 | Lundquist |
| 7,745,129 B1 | 6/2010 | Schatz |
| 7,771,973 B2 | 8/2010 | Milton |
| 7,785,796 B2 | 8/2010 | Balasubramanian |
| 7,795,424 B2 | 9/2010 | Liu |
| 7,816,503 B2 | 10/2010 | Milton |
| 7,835,871 B2 | 11/2010 | Kain |
| 7,843,567 B2 | 11/2010 | Moon |
| 7,883,869 B2 | 2/2011 | Ju |
| 7,888,073 B2 | 2/2011 | Densham |
| 7,897,345 B2 | 3/2011 | Lapidus |
| 7,993,895 B2 | 8/2011 | Eid |
| 7,994,304 B2 | 8/2011 | Siddiqi |
| 7,998,717 B2 | 8/2011 | Eid |
| 8,012,690 B2 | 9/2011 | Berka |
| 8,018,593 B2 | 9/2011 | Tan |
| 8,022,194 B2 | 9/2011 | Piepenburg |
| 8,030,466 B2 | 10/2011 | Shin |
| 8,031,918 B2 | 10/2011 | Roth |
| 8,032,310 B2 | 10/2011 | Stenger |
| 8,053,192 B2 | 11/2011 | Bignell |
| 8,058,414 B2 | 11/2011 | Menchen |
| 8,071,346 B2 | 12/2011 | Eid |
| 8,071,739 B2 | 12/2011 | Milton |
| 8,084,590 B2 | 12/2011 | Milton |
| 8,088,575 B2 | 1/2012 | Ju |
| 8,094,312 B2 | 1/2012 | Ulmer |
| 8,116,988 B2 | 2/2012 | Glick |
| 8,143,599 B2 | 3/2012 | Feng |
| 8,148,503 B2 | 4/2012 | Litosh |
| 8,158,346 B2 | 4/2012 | Balasubramanian |
| 8,178,360 B2 | 5/2012 | Barnes |
| 8,182,993 B2 | 5/2012 | Tomaney |
| 8,209,130 B1 | 6/2012 | Kennedy |
| 8,212,020 B2 | 7/2012 | Benner |
| 8,236,532 B2 | 8/2012 | Ronaghi |
| 8,241,573 B2 | 8/2012 | Banerjee |
| 8,247,177 B2 | 8/2012 | Smith |
| 8,263,364 B2 | 9/2012 | Williams |
| 8,263,365 B2 | 9/2012 | Williams |
| 8,271,206 B2 | 9/2012 | Liu |
| 8,280,640 B2 | 10/2012 | Levin |
| 8,298,792 B2 | 10/2012 | Ju |
| 8,299,226 B2 | 10/2012 | Piepenburg |
| 8,300,971 B2 | 10/2012 | Osher |
| 8,301,394 B2 | 10/2012 | Chen |
| 8,370,079 B2 | 2/2013 | Sorenson |
| 8,383,039 B2 | 2/2013 | Zhou |
| 8,394,586 B2 | 3/2013 | Balasubramanian |
| 8,399,188 B2 | 3/2013 | Zhao |
| 8,399,196 B2 | 3/2013 | Hoser |
| 8,407,012 B2 | 3/2013 | Erlich |
| 8,407,554 B2 | 3/2013 | Kermani |
| 8,427,637 B2 | 4/2013 | Gao |
| 8,429,108 B2 | 4/2013 | Eusterbrock |
| 8,460,865 B2 | 6/2013 | Chee |
| 8,463,718 B2 | 6/2013 | Ben-Hur |
| 8,481,259 B2 | 7/2013 | Gordon |

(56) References Cited

U.S. PATENT DOCUMENTS

| | | |
|---|---|---|
| 8,481,903 B2 | 7/2013 | Triener |
| 8,594,951 B2 | 11/2013 | Homer |
| 8,612,161 B2 | 12/2013 | Gordon |
| 8,666,678 B2 | 3/2014 | Davey |
| 8,703,422 B2 | 4/2014 | Tomaney |
| 8,725,425 B2 | 5/2014 | Heiner |
| 8,728,399 B2 | 5/2014 | Jaffe |
| 8,738,300 B2 | 5/2014 | Porreca |
| 8,748,789 B2 | 6/2014 | Triener |
| 8,774,494 B2 | 7/2014 | Staker |
| 8,795,971 B2 | 8/2014 | Kersey |
| 8,812,268 B2 | 8/2014 | Scoullar |
| 8,831,316 B2 | 9/2014 | Tyurina |
| 8,852,910 B2 | 10/2014 | Smith |
| 8,886,535 B2 | 11/2014 | Chong |
| 8,900,810 B2 | 12/2014 | Gordon |
| 8,929,630 B2 | 1/2015 | Fu |
| 8,934,098 B2 | 1/2015 | Cox |
| 8,940,481 B2 | 1/2015 | Gordon |
| 8,965,076 B2 | 2/2015 | Garcia |
| 2001/0030290 A1 | 10/2001 | Stern |
| 2002/0004204 A1 | 1/2002 | OKeefe |
| 2002/0110899 A1 | 8/2002 | Wheatcroft |
| 2003/0087289 A1 | 5/2003 | Zuzan |
| 2003/0112432 A1* | 6/2003 | Yguerabide ........... G01N 21/47 356/317 |
| 2003/0215816 A1 | 11/2003 | Sundararajan |
| 2003/0224419 A1 | 12/2003 | Corcoran |
| 2004/0002073 A1 | 1/2004 | Li |
| 2004/0029126 A1 | 2/2004 | Bloecker |
| 2004/0142347 A1 | 7/2004 | Stockwell |
| 2004/0152108 A1 | 8/2004 | Keith |
| 2004/0175718 A1 | 9/2004 | Chee |
| 2004/0185466 A1 | 9/2004 | Ju |
| 2004/0229269 A1 | 11/2004 | Hashmi |
| 2004/0234114 A1* | 11/2004 | Amakawa .......... G01N 21/6452 382/128 |
| 2005/0019902 A1 | 1/2005 | Mathies |
| 2005/0026163 A1 | 2/2005 | Sundararajan |
| 2005/0052509 A1 | 3/2005 | Gilligan |
| 2005/0064469 A1 | 3/2005 | Schulz |
| 2005/0170367 A1 | 8/2005 | Quake |
| 2005/0211874 A1 | 9/2005 | Takeyama et al. |
| 2005/0227231 A1 | 10/2005 | Tcherkassov |
| 2005/0239085 A1 | 10/2005 | Buzby |
| 2005/0244827 A1 | 11/2005 | Olsson |
| 2006/0034543 A1 | 2/2006 | Bacus et al. |
| 2006/0073493 A1 | 4/2006 | Fasulo |
| 2006/0105349 A1 | 5/2006 | Ekenberg |
| 2006/0147935 A1 | 7/2006 | Linnarsson |
| 2006/0166203 A1 | 7/2006 | Tooke |
| 2006/0240439 A1 | 10/2006 | Smith |
| 2006/0275782 A1 | 12/2006 | Gunderson |
| 2006/0281109 A1 | 12/2006 | BarrOst |
| 2007/0048748 A1 | 3/2007 | Williams |
| 2007/0070349 A1 | 3/2007 | Harris |
| 2007/0082358 A1 | 4/2007 | Fuerst |
| 2007/0117103 A1 | 5/2007 | Buzby |
| 2007/0117104 A1 | 5/2007 | Buzby |
| 2007/0177799 A1 | 8/2007 | Tyurina |
| 2007/0196832 A1 | 8/2007 | Efcavitch |
| 2007/0196846 A1 | 8/2007 | Hanzel |
| 2008/0038839 A1 | 2/2008 | Linder |
| 2008/0087826 A1 | 4/2008 | Harris |
| 2008/0088823 A1 | 4/2008 | Harris |
| 2008/0103053 A1 | 5/2008 | Siddiqi |
| 2008/0138804 A1 | 6/2008 | Buzby |
| 2008/0161194 A1 | 7/2008 | Turner |
| 2008/0161195 A1 | 7/2008 | Turner |
| 2008/0176241 A1 | 7/2008 | Eid |
| 2008/0182757 A1 | 7/2008 | Heiner |
| 2008/0246949 A1 | 10/2008 | Harris |
| 2008/0280773 A1 | 11/2008 | Fedurco |
| 2008/0293071 A1 | 11/2008 | Gelfand |
| 2009/0056390 A1 | 3/2009 | Falkensson |
| 2009/0099027 A1 | 4/2009 | Greiner |
| 2009/0155793 A1 | 6/2009 | Oliphant |
| 2009/0186771 A1 | 7/2009 | Siddiqi |
| 2009/0263791 A1 | 10/2009 | Ju |
| 2009/0298131 A1 | 12/2009 | Gordon et al. |
| 2009/0325260 A1 | 12/2009 | Otto |
| 2010/0009871 A1 | 1/2010 | Reed |
| 2010/0015611 A1 | 1/2010 | Webster |
| 2010/0035253 A1 | 2/2010 | Gordon |
| 2010/0035273 A1 | 2/2010 | Axen |
| 2010/0036110 A1 | 2/2010 | Xie |
| 2010/0041029 A1 | 2/2010 | Ju |
| 2010/0063742 A1 | 3/2010 | Hart |
| 2010/0063743 A1 | 3/2010 | Gordon |
| 2010/0087327 A1 | 4/2010 | Weng |
| 2010/0121582 A1 | 5/2010 | Pan |
| 2010/0143932 A1 | 6/2010 | Lapidus |
| 2010/0152050 A1 | 6/2010 | Gordon et al. |
| 2010/0153420 A1 | 6/2010 | Yang |
| 2010/0159531 A1 | 6/2010 | Gordon |
| 2010/0167413 A1 | 7/2010 | Lundquist |
| 2010/0227327 A1 | 9/2010 | Xie |
| 2010/0235105 A1 | 9/2010 | Volkov |
| 2010/0246977 A1 | 9/2010 | Fu |
| 2010/0311061 A1 | 12/2010 | Korlach |
| 2010/0323350 A1 | 12/2010 | Gordon et al. |
| 2010/0330569 A1 | 12/2010 | Olejnik |
| 2011/0014611 A1 | 1/2011 | Ju |
| 2011/0045489 A1 | 2/2011 | Gardner |
| 2011/0052446 A1 | 3/2011 | Hirano |
| 2011/0081647 A1 | 4/2011 | Siddiqi |
| 2011/0087016 A1 | 4/2011 | Suo |
| 2011/0124054 A1 | 5/2011 | Olejnik |
| 2011/0127444 A1* | 6/2011 | Ozasa ................. G01N 15/147 250/458.1 |
| 2011/0212437 A1 | 9/2011 | Emig |
| 2011/0220775 A1 | 9/2011 | Triener |
| 2011/0251828 A1 | 10/2011 | Scoullar |
| 2011/0254969 A1 | 10/2011 | Tyurina |
| 2011/0256631 A1 | 10/2011 | Tomaney |
| 2011/0257889 A1 | 10/2011 | Klammer |
| 2011/0268347 A1 | 11/2011 | Staker |
| 2011/0300534 A1 | 12/2011 | Chiou |
| 2012/0020537 A1 | 1/2012 | Garcia |
| 2012/0041727 A1 | 2/2012 | Mishra |
| 2012/0052490 A1 | 3/2012 | Eid |
| 2012/0088691 A1* | 4/2012 | Chen ....................... B01L 7/52 506/12 |
| 2012/0092477 A1 | 4/2012 | Kawano et al. |
| 2012/0095201 A1 | 4/2012 | Milton |
| 2012/0109598 A1 | 5/2012 | Davey |
| 2012/0116688 A1 | 5/2012 | Mishra |
| 2012/0156680 A1 | 6/2012 | Ju |
| 2012/0173159 A1 | 7/2012 | Davey |
| 2012/0197623 A1 | 8/2012 | Homer |
| 2012/0252010 A1 | 10/2012 | Balasubramanian |
| 2012/0258869 A1 | 10/2012 | Kersey |
| 2012/0270305 A1 | 10/2012 | Reed |
| 2012/0282708 A1 | 11/2012 | Corbett |
| 2012/0330566 A1 | 12/2012 | Chaisson |
| 2013/0053280 A1 | 2/2013 | Hamasaki |
| 2013/0054171 A1 | 2/2013 | Chen |
| 2013/0060482 A1 | 3/2013 | Sikora |
| 2013/0096015 A1 | 4/2013 | Ju |
| 2013/0116128 A1 | 5/2013 | Shen |
| 2013/0116130 A1 | 5/2013 | Fu |
| 2013/0122485 A1 | 5/2013 | Hong |
| 2013/0137091 A1 | 5/2013 | Gordon |
| 2013/0137110 A1 | 5/2013 | Kraihanzel |
| 2013/0138358 A1 | 5/2013 | Tang |
| 2013/0217006 A1 | 8/2013 | Sorenson |
| 2013/0235388 A1 | 9/2013 | Segale |
| 2013/0260372 A1 | 10/2013 | Buermann |
| 2013/0281321 A1 | 10/2013 | Mann |
| 2013/0289921 A1 | 10/2013 | Gopalan |
| 2013/0301888 A1 | 11/2013 | Gordon |
| 2013/0303384 A1 | 11/2013 | Rearick |
| 2014/0051584 A1 | 2/2014 | Davey |
| 2014/0073514 A1 | 3/2014 | Shen |

(56) References Cited

U.S. PATENT DOCUMENTS

| | | |
|---|---|---|
| 2014/0073517 A1 | 3/2014 | Zhou |
| 2014/0220558 A1 | 8/2014 | Homer |
| 2014/0222399 A1 | 8/2014 | Davey |
| 2014/0235461 A1 | 8/2014 | Yin |
| 2014/0248618 A1 | 9/2014 | Shaikh |
| 2014/0303016 A1 | 10/2014 | Tomaney |
| 2014/0309143 A1 | 10/2014 | Kersey |
| 2014/0315328 A1 | 10/2014 | Lee |
| 2014/0329694 A1 | 11/2014 | Buermann |
| 2014/0356884 A1 | 12/2014 | Mittal |
| 2015/0038339 A1 | 2/2015 | Gordon |
| 2015/0045234 A1 | 2/2015 | Stone |
| 2015/0080231 A1 | 3/2015 | Staker |
| 2015/0080232 A1 | 3/2015 | Ju |
| 2015/0099642 A1 | 4/2015 | Barany |

FOREIGN PATENT DOCUMENTS

| | | |
|---|---|---|
| WO | 0058507 | 10/2000 |
| WO | 02093144 | 11/2002 |
| WO | 2004018493 | 3/2004 |
| WO | 2004018497 | 3/2004 |
| WO | 2004042403 | 5/2004 |
| WO | 2006074351 | 7/2006 |
| WO | 2008037568 | 4/2008 |
| WO | 2008134867 | 11/2008 |
| WO | 2009085328 | 7/2009 |
| WO | 2011011738 | 1/2011 |
| WO | 2014055963 | 4/2014 |
| WO | 2014165554 | 10/2014 |

OTHER PUBLICATIONS

Entire patent prosecution history of U.S. Appl. No. 13/802,957, filed Mar. 14, 2013, entitled, "Apparatus and Methods for Purging Flow Cells in Nucleic Acid Sequencing Instruments."
International Search Report and Written Opinion for PCT International Application No. PCT/US2014/23474 dated Jul. 14, 2014.
PCT International Search Report and Written Opinion for PTC Application No. PCT/US2014/023490 dated Sep. 24, 2015.
Supplemental European Search Report for European Application No. EP14767413 dated Oct. 31, 2016, 8 pages.

* cited by examiner

FLOW CELL ALIGNMENT METHODS AND SYSTEMS

BACKGROUND OF THE INVENTION

Over the past 25 years, the amount of DNA sequence information generated and deposited into Genbank has grown exponentially. Many of the next-generation sequencing technologies use a form of sequencing by synthesis (SBS), wherein specially designed nucleotides and DNA polymerases are used to read the sequence of chip-bound, single-stranded DNA templates in a controlled manner. Other next-generation sequencing technologies may use native nucleotides and/or polymerases or labeled oligonucleotides and ligation enzymes to determine nucleic acid sequences. To attain high throughput, many millions of such template spots, each being either single or multiple molecules, are arrayed across a sequencing chip and their sequence is independently read out and recorded. The desire to perform high throughput sequencing stems from the need for faster processing and reduced costs. However, commercial high throughput systems, while reducing the cost of large scale sequencing (e.g., 10-100 gigabases), make smaller scale sequencing (e.g., 100 megabases to 1 gigabase) costly and inconvenient.

Recently, instruments have been developed to perform sequencing on a much smaller scale than conventional devices. Exemplary apparatus and methods that may be used for performing smaller scale sequencing operations are described in U.S. Patent Publication Nos. 2010/0323350 (application Ser. No. 12/719,469, field Mar. 8, 2010), 2010/0152050 (application Ser. No. 12/704,842, field Feb. 12, 2010), and 2009/0298131 (application Ser. No. 12/370,125, field Feb. 12, 2009). The foregoing are incorporated herein by reference. Such instruments use an "assembly line" type system, which may be arranged in the form of a carousel, to simultaneously process a number of relatively small flow cells containing single-stranded DNA templates. During operation, each flow cell is physically moved through a series of processing stations. Some of these processing stations purge the flow cell and fill it with a new reagent, while others are used for imaging the flow cell, or as idle stations where the flow cell is held without substantive processing. Other processing stations may also be provided. These instruments provide high throughput SBS operations, while offering significant savings in reagents and other processing costs. This new generation of instruments is expected to expand the public's access to SBS operations to use for various purposes, at a reduced cost, and with more rapid turnaround than earlier devices could offer.

There continues to be a need to advance the state of the art of sequencing instruments, and particularly those that use movable flow cells for small-scale sequencing operations.

SUMMARY

The present invention is embodied in imagers and alignment methods for use by imagers imaging deoxyribonucleic acid (DNA) fragments on a flow cell are disclosed. The imagers capture intensity values at DNA fragment bead locations in tiles with each tile having a reference location in the flow cell.

Flow cells may be aligned by obtaining a dark field image of each tile during a first imaging session, identifying a first dark field constellation of bead locations within a first tile and a second dark field constellation of bead locations within a second tile during the first imaging session, identifying constellations corresponding to the first and second dark field constellations during a second imaging session, altering the reference location of at least one tile during the second imaging session to correct for a linear offset in the corresponding first dark field constellations, and applying at least one correction factor for reading out intensity values from the imager for the bead locations in the flow cell to correct for an angular offset determined from offsets in the corresponding first and second dark field constellations.

An imager may include an xy stage supporting the flow cell, a camera configured to capture images of flow cell tiles, and a processor coupled to the xy stage and the camera. The processor may be configured to position the XY stage and control the camera to obtaining a dark field image of each tile during a first imaging session, identify a first dark field constellation of bead locations within a first tile and a second dark field constellation of bead locations within a second tile during the first imaging session, identify constellations corresponding to the first and second dark field constellations during a second imaging session, alter the reference location of at least one tile during the second imaging session when positioning the XY stage to correct for a linear offset in the corresponding first dark field constellations, and apply at least one correction factor for reading out intensity values from the camera for the bead locations in the flow cell to correct for an angular offset determined from offsets in the corresponding first and second dark field constellations.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. Lines without arrows connecting components may represent a bi-directional exchange between these components. This emphasizes that according to common practice, the various features of the drawings are not drawn to scale. On the contrary, the dimensions of the various features are arbitrarily expanded or reduced for clarity. Included in the drawings are the following figures.

DETAILED DESCRIPTION OF THE INVENTION

Figure 1:
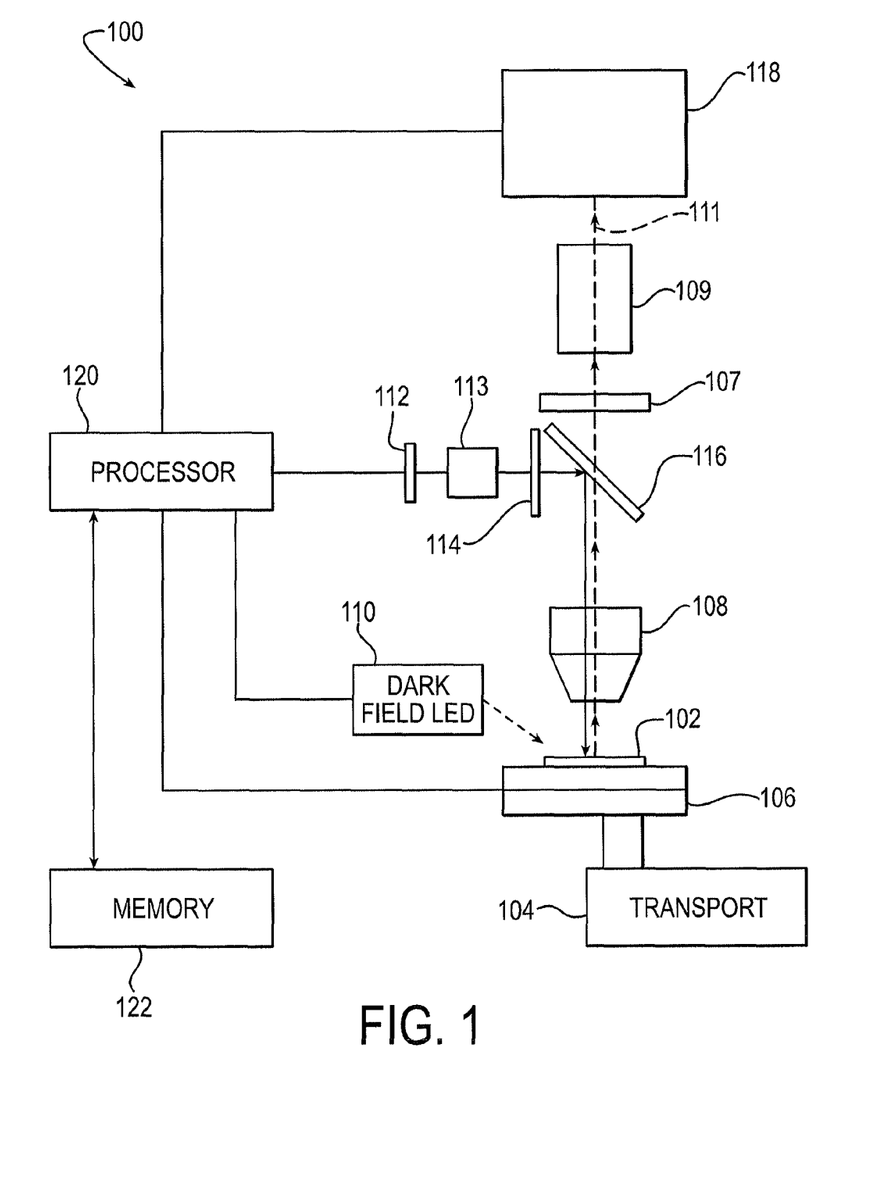
FIG. 1 is a block diagram of an imager in accordance with aspects of the present invention.

FIG. 1 depicts an imager 100 for imaging bead locations of deoxyribonucleic acid (DNA) fragments on a flow cell of a chip 102 in accordance with one embodiment of the present invention. As will be discussed in further detail below, the imager 100 images the flow cell in tiles with each tile having a reference location in the flow cell. A transport 104 and an xy stage 106 position the chip 102 for imaging by the imager 100. The transport 104 moves the XY stage 106 to remove the chip from a carousel or other type of conveyor system and position the chip for imaging within the imager 100. The xy stage 106 positions the chip 102 in a horizontal plane under an objective lens 108 for imaging of individual tiles.

The imager 100 includes one or more dark field LEDs 110 and at least one bank of florescent LEDs 112 to illuminate the DNA fragments on the flow cell. In the illustrated embodiment, the dark field LED 110 illuminates the chip 102 from the side and the florescent field LEDs 112 illuminate the chip 102 from above through a lens 113, an excitation filter 114, and a dichroic mirror 116. The dichroic mirror 116 reflects light in one or more frequency bands and passes light not in those frequency band(s). The dark field LED 110 may be a red LED. The florescent field LEDs 112 and corresponding filters 114 may be selected to illuminate the chip 102 with desired colors of light.

When the dark field LEDs 110 are used to illuminate the chip, the mirror 116 may be removed from the pathway such that light reflected by the bead locations in the flow cell along an imaging axis 111 passes though the objective lens 108, an emission filter 109, and a lens system 109. The light then impinges upon a camera 118 where it is captured. When the florescent field LEDs 112 are used, light from the LEDs 112 pass through the filter 114 and are reflected by the mirror 116 through the objective lens 108 toward the chip 102. The bead locations emit light in response to being illuminated by light from the florescent field LEDs 112 (with the emitted light having a different wavelength). The emitted light may be produced by fluorescing dyes or other compositions associated with particular nucleotides, as described in U.S. application Ser. No. 12/719,469. The emitted light passes through the objective lens 108, the mirror 116, the emission filter 107, and the lens system 109 to impinge on the camera 118. The camera may be 3296 by 2472 charge coupled device (CCD). Although one bank of florescent field LEDs 112 is illustrated, additional banks of LEDs and corresponding filters may be employed to illuminate the chip with different colors of light. For example, four different colors of light may be produced, e.g., blue, green, yellow, and red.

A processor 120 is coupled to the various components to control the positioning of the chip and the imaging of the flow cell on the chip. A memory 122 is coupled to the processor 120. The processor 120 may control the imaging system 100 to implement one or more of the steps described herein. The memory is a non-transitory computer readable medium that may store instructions that, when carried out by the processor 120, implement one or more of the steps described herein. Additionally, the memory may store image information from camera 118 such as intensity values at bead locations obtained during imaging.

Figure 2:
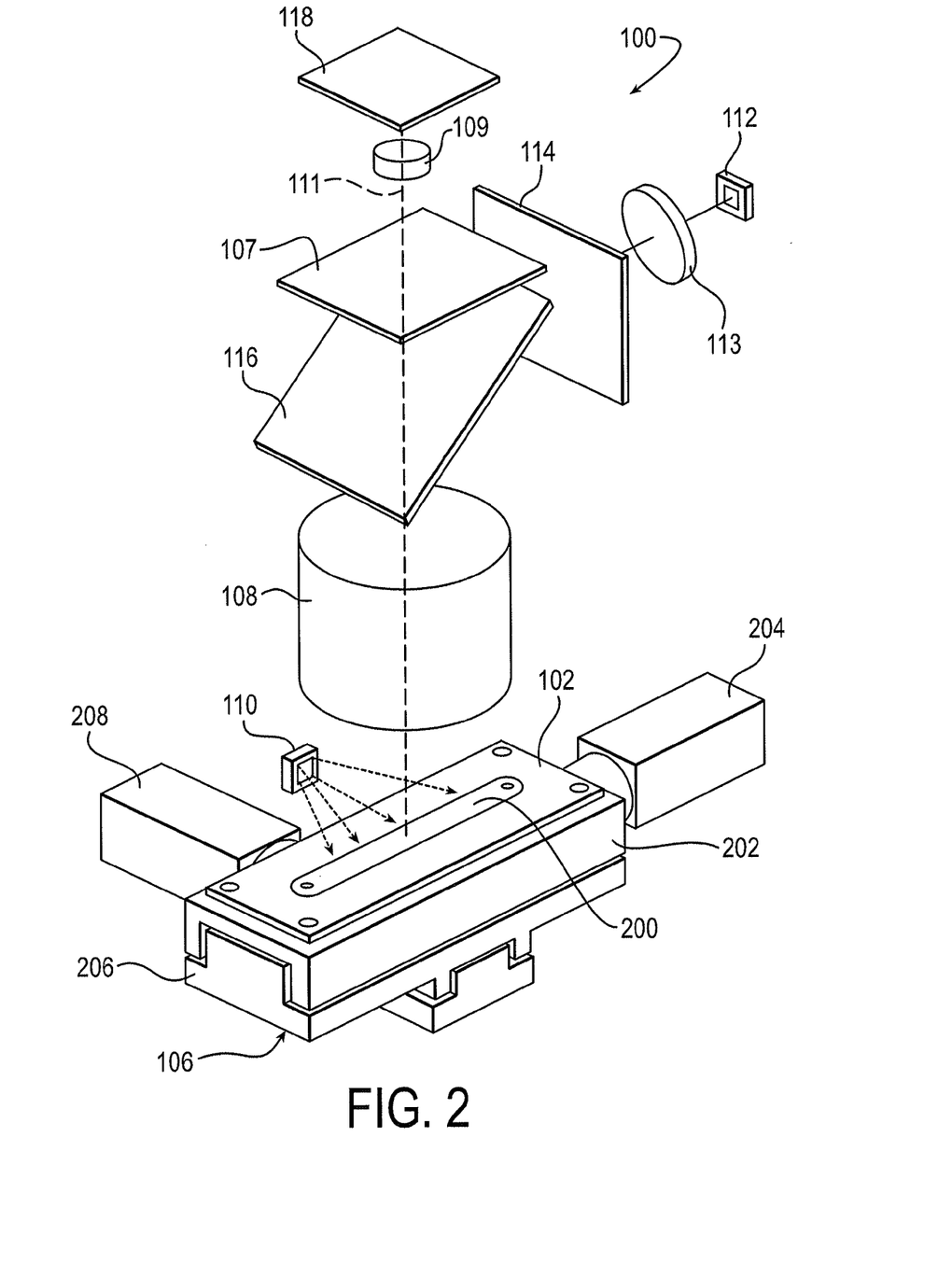
FIG. 2 a perspective view of an imager in accordance with aspects of the present invention.

FIG. 2 is a perspective view of the imaging system 100 depicting the xy stage 106 with the chip 102 thereon in greater detail. The chip 102 includes a flow cell 200 containing DNA fragments. The xy stage 106 includes an x-stage 202 and corresponding controller 204 and a y-stage 206 and corresponding controller 208. The processor 120 (FIG. 1) is coupled to the x-controller 204 and the y-controller 208. The processor 120 controls the x-controller 204 to move the x-stage 200 (and thereby the flow cell) along a first axis (referred to herein as the x-axis) perpendicular to an imaging axis 111. The processor 120 additionally controls the y-controller 208 to move the y-stage 206 (and thereby the flow cell 200) along a second axis (referred to herein as the y-axis) perpendicular to the imaging axis 111 and to the first axis.

Figure 3:
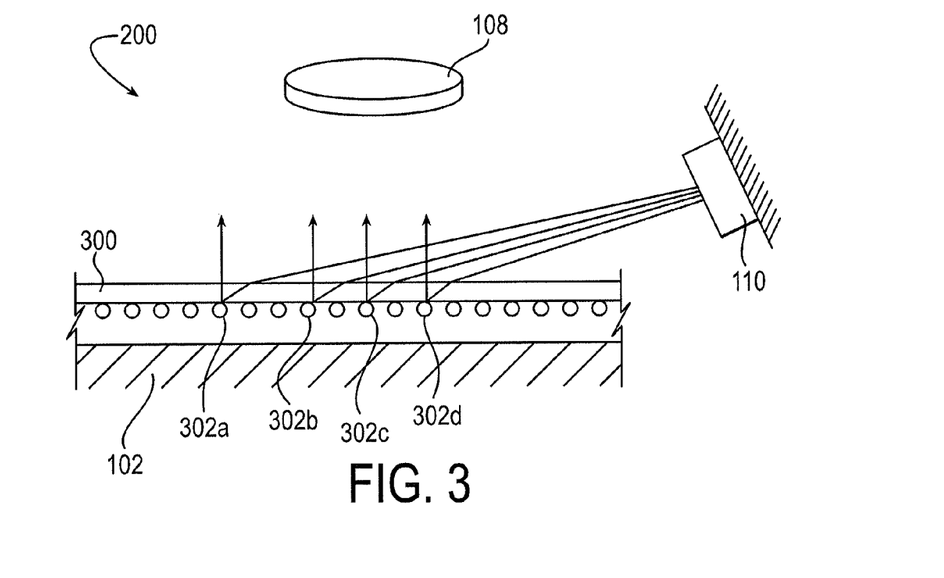
FIG. 3 is a side view of a flow cell within the imager of FIG. 2 illustrating DNA fragment beads reflecting dark field LED light.

FIG. 3 depicts a cutaway of a portion a chip 102 being illuminated by the dark field LED 110. The flow cell 200 includes a transparent layer 300 including DNA fragments thereon. The transparent layer 300 may be glass. The DNA fragments reflect light from the dark field LED 110 through the objective lens 108 (FIG. 1) toward the camera 118, which identifies their location. These locations of DNA fragments are referred to herein as bead locations. FIG. 3 depicts four bead locations (302a, b, c, d) although in actual use there will be many orders of magnitude more bead locations per tile. As illustrated in FIG. 3, the dark field LED 110 may be tilted to optimize illumination of the beads. In an embodiment, the objective lens 108 and the dark field LED 112 are stationary in the x,y plane so that the bead illumination incidence angle does not change.

Figure 4:
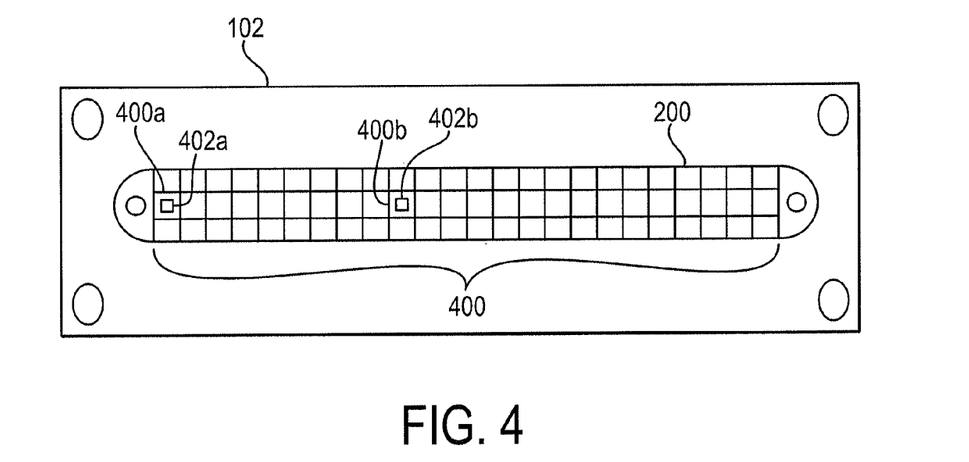
FIG. 4 is a top view of a flow cell within the imager of FIG. 2 illustrating virtual tiles for imaging the flow cell.

FIG. 4 depicts a top view of a chip 102. The chip includes a flow cell 200. During imaging, the flow cell 200 is imaged in tiles 400. In the illustrated embodiment, the flow cell 200 is imaged using 72 tiles (three rows of 24 tiles). Each tile has a reference location corresponding to the position of the tile on the chip. As will be described in further detail below, at least two tiles, e.g., tile 400a and 400b, may be selected for use in aligning the flow cell 200 and registering image intensities captured for individual tiles 400 within the flow cell 200 during imaging. The at least two tiles may be located essentially anywhere within the flow cell. In an embodiment, the tiles are in a center row and are at least 5 tiles away from one another, e.g., 9 tiles away from one another.

A reference constellation of bead locations within each tile, e.g., 402a and 402b, may be used for alignment and registration purposes. In one embodiment, one reference constellation 402a is used to determine an offset for the tile reference locations when the flow cell has been removed from the imager 100 and added back in for a subsequent imaging session. Two or more reference constellations may be used in other embodiments. Additionally, the difference in the offsets for two constellations may be used to calculate an angular adjustment for bead locations when reading out intensity values.

Figure 5:
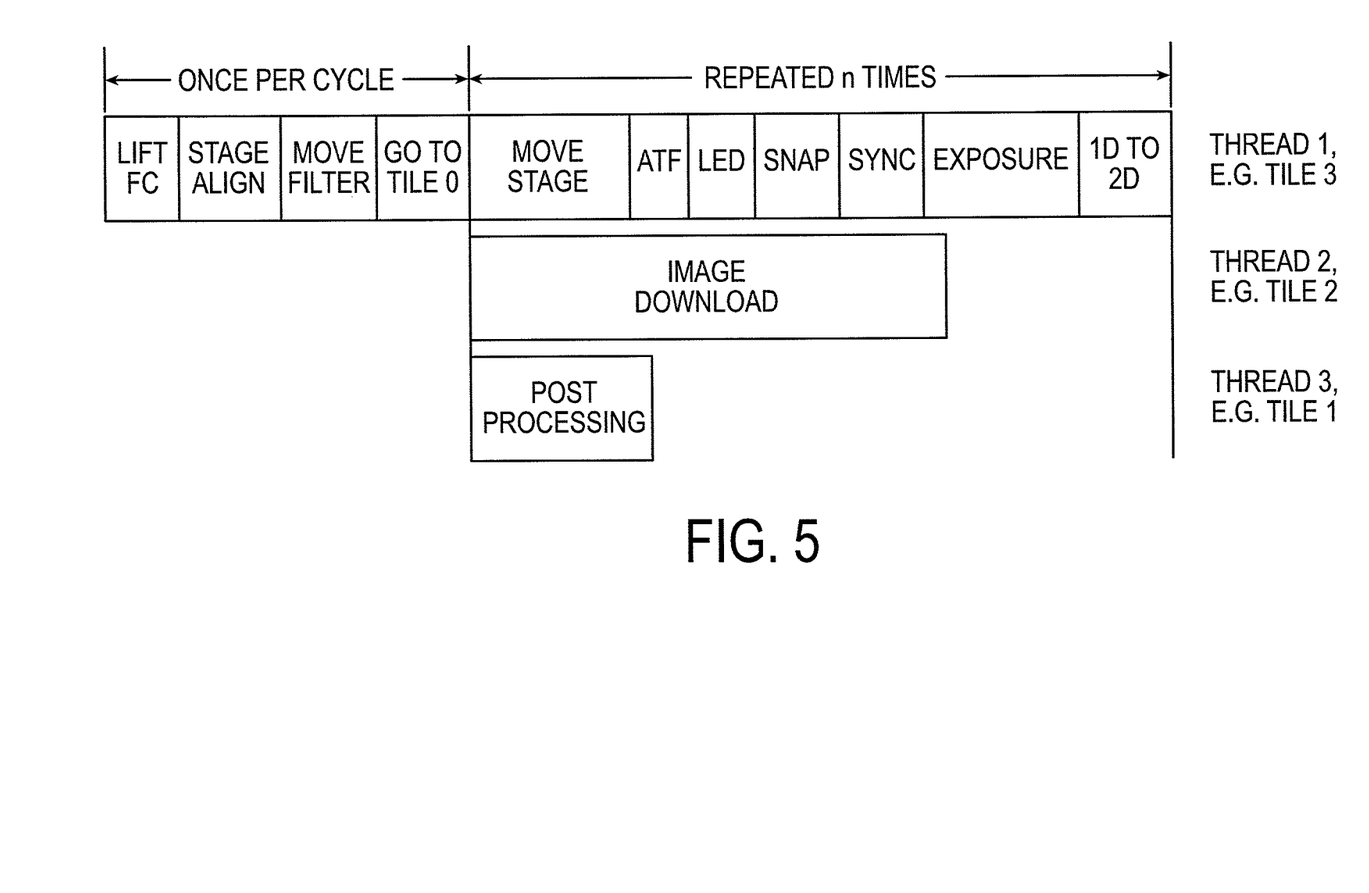
FIG. 5 is a timing diagram for imaging a flow cell in accordance with aspects of the present invention.
Figure 6:
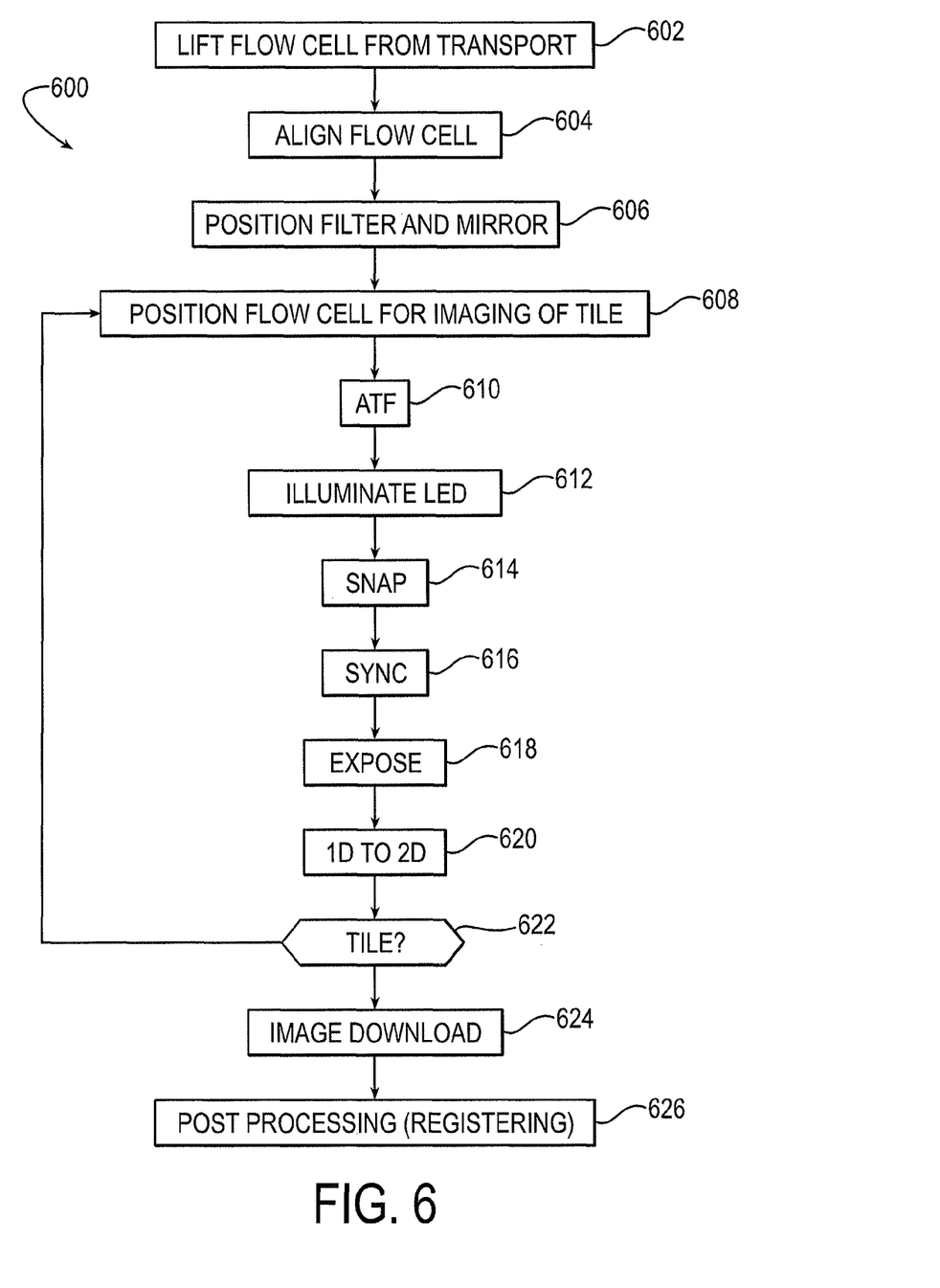
FIG. 6 is a flow chart of steps for imaging a flow cell in accordance with aspects of the present invention.

FIG. 5 depicts a timing diagram 500 and FIG. 6 depicts a flow chart 600 for imaging a flow cell in accordance with aspects of the present invention. Although the timing diagram and flow chart are described with reference to FIGS. 1-4, other suitable apparatus for carrying out the steps described herein will be understood by one of skill in the art from the description herein and are considered within the scope of the present invention. Additionally, one or more of the steps described herein may be omitted or performed in a different order without departing from the spirit and scope of the present invention. The total time for imaging all tiles in a flow cell may be on the order of 6 minutes.

At step 602, a flow cell (FC) is lifted from a flow cell carrier such as a carousel. The flow cell may be lifted by a transport 104 into position under an objective lens 108 of an imager 100 for imaging during an imaging sequence. It may take approximately 7 seconds for the transport to move the flow cell from the carrier to the imager 100 for imaging.

At block 604, the flow cell is aligned within the imager. If it is the first time the flow cell is positioned within the imager, a dark field image of a first tile, e.g., tile 400a, and a second tile, e.g., tile 400b, is obtained and a subset of the beads in each image is identified (referred to herein as a constellation; e.g., constellations 402a and 402b). Thereafter, in subsequent imaging sessions, a dark field image of the first tile and the second tile is obtained and the dark field images from the current session are compared to the dark field images from the first imaging session to identify matching constellations and to determine a corresponding difference in position. The difference in position between the constellations from at least one tile may then be used to alter the reference positions of each tile for the current imaging session. Additionally, dark field images for all the tiles may be obtained at this stage. It may take approximately 29 seconds or more to align the stage and obtain the dark field images.

At block 606, a filter and mirror are positioned for florescent field imaging. The processor 102 may control the positioning of the filter 114 and mirror 116, e.g., though an additional transport device (not shown). It may take approximately 4 seconds to move the filter and the mirror.

At block 608, the flow cell is positioned for imaging of a particular tile, e.g., tile 0 located in the upper left hand corner of the tiles 400 (FIG. 4). The processor 102 may position the flow cell for imaging through the use of the x-controller 204 and the y-controller 208 (FIG. 2) to move the flow cell to the reference position corresponding to the desired tile as altered in block 604. It may take approximately 7 seconds to position the flow cell at the first tile. Thereafter, it may take a little over 0.5 second to move to the next tile to be imaged.

At block 610, the imaging system 100 autofocuses (ATF) to create a sharp image of the flow cell tile on the camera. The processor 120 may perform autofocussing by adjusting the position of the camera 118, objective lens 108, or the chip 102 (e.g., via the transport 104 (FIG. 1)) along the imaging axis 111. It may take approximately 0.25 seconds to perform autofocussing.

At block 612, the florescent LEDs are turned on. The processor 120 may turn on the fluorescent LEDs 112. It may take approximately 120 milliseconds to turn on the LEDs 112.

At block 614, the camera is triggered (snap) and, at block 616, the imaging system is synchronized. The processor 120 may trigger the camera 118 to take an image and synchronize itself with the camera 118. It may take approximately 110 milliseconds to trigger the camera 118 and approximately 200 milliseconds to synchronize.

At block 618, the camera images the florescent light from the flow cell tile (exposure time). The camera 118 may have an exposure period of 350 milliseconds during which light from the flow cell is captured.

At block 620, an optional conversion step is performed to covert the imaged from a 1-dimensional (1D) array to a 2-dimensional (2D) array. Processor. 120 may perform the conversion. This step may be performed as a programming convenience and may be omitted. It may take approximately 43 milliseconds to perform the conversion.

At block 622, a decision is made regarding tiles to be processed. If there are additional tiles to process, processing proceeds at block 608 with the next tile and, in parallel, processing proceeds at block 624 with further processing of the light captured from the current tile. If there are no additional tiles, processing proceeds only at block 624.

At block 624, the image is downloaded from the camera. The processor 120 may download the image from the camera 118, e.g., into random access memory (RAM) associated with the processor. It may take approximately 700 milliseconds to download the image.

At block 626, post processing of the downloaded image is performed. Processor 120 may perform the processing and store the result in memory 122. The post processing may involve registration of the captured images with the bead locations determined from the dark field image as adjusted based on offsets determined at block 604. It may take approximately 365 milliseconds to register the images with the bead locations and approximately 25 milliseconds to extract the pixels, e.g., for storage in memory 122.

Figure 7:
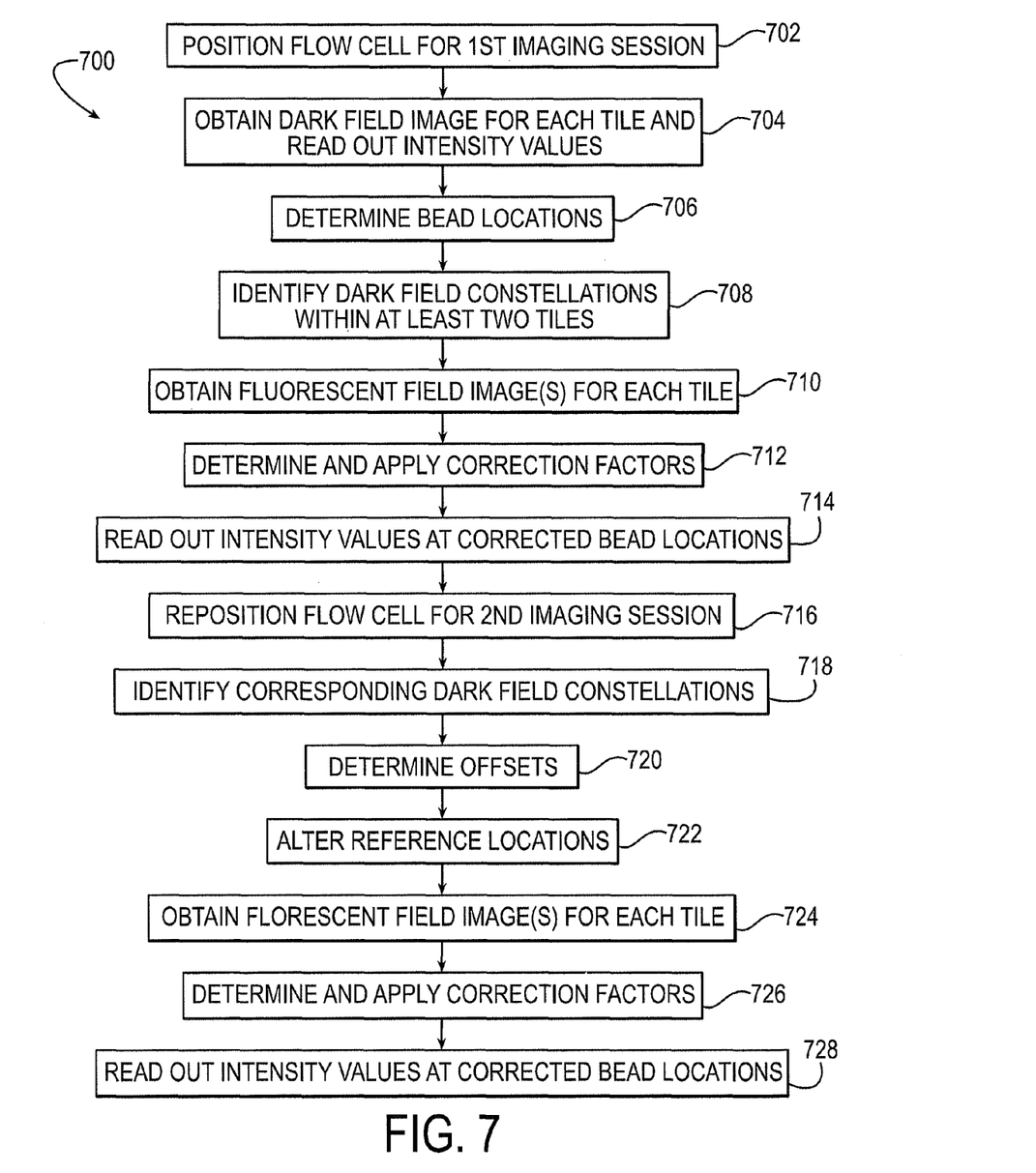
FIG. 7 is a flow chart of steps for altering tile reference locations and registering DNA fragment bead locations in accordance with aspects of the present invention.

FIG. 7 depicts a flow chart 700 of steps describing the alignment of flow cells and the registration of captured images in further detail in accordance with aspects of the present invention. Although flow chart 700 is described with reference to FIGS. 1-4, other suitable apparatus for carrying out the steps described herein will be understood by one of skill in the art from the description herein and are considered within the scope of the present invention. Additionally, one or more of the steps described herein may be omitted or performed in a different order without departing from the spirit and scope of the present invention.

At block 702, a flow cell is positioned for a first imaging session. A flow cell 200 on a chip 102 may be lifted by a transport 104 into position under an objective lens 108 of an imager 100 under control of processor 120 for imaging during the first imaging session.

At block 704, a dark field image is obtained and intensity values are read out for each tile in the flow cell to be imaged. In one embodiment, a dark field image is first obtained for two reference tiles 400 within the flow cell 200 and a dark field image for all tiles 400 is subsequently obtained. In another embodiment, a dark field image for all tiles 400 is initially obtained without separately obtaining another dark field image for the two reference tiles.

The dark field image for each tile 400 may be obtained by moving the flow cell 200 to a first reference location associated with a first tile using an xy-stage 106 under control of the processor 120, illuminating the side of the flow cell 200 with a dark field LED 110, capturing light reflected by the DNA fragments with a camera 118, and storing intensity values in a memory 122 (with relatively high intensity values representing the locations of the DNA fragment bead locations). Subsequent tiles within the flow cell may then be imaged by iteratively moving the flow cell to a respective reference location associated with each of those tiles and repeating the capturing process. During the first imaging session for each flow cell, the reference locations for the tiles may be nominal locations established based on a standard flow geometry and xy-stage 106 positions. For example, the xy-stage 106 may start at a "home" location at one limit of the x and y travel range, and each nominal location may be predetermined as an x and y distance from the home location that is expected to place the center of each tile directly under the objective lens 108. In this example, tile 0 may have a nominal location stored in a lookup table as ($x_0$, $y_0$), where $x_0$ is a distance from the home x location, and $y_0$ is a distance from the home y location, and each other tile may have its own nominal location stored in a similar manner (distances may be measured as distances, motor movement increments, and so on).

At block 706, bead locations are determined. The locations within the dark field image having a relatively high intensity value, represent the bead locations within the flow cells. The bead locations (representing the location of the DNA fragments) may be determined by analyzing the intensity values from the dark field image with the processor 120 and selecting those with an intensity value above a value indicating the presence of a bead. After each bead is located in the dark field, the x and y locations of the bead are stored and used in later imaging steps as expected bead locations. For example, an array of x,y locations corresponding to each bead may be saved for each tile. Having identified the bead locations in terms of x and y locations, the full-resolution image itself may optionally be discarded.

At block 708, dark field reference constellations are identified within at least two tiles. In an embodiment, the processor 120 identifies two dark field reference constellations—a first dark field reference constellation within a first tile and a second dark field reference constellation within a second tile. Each dark field reference constellation includes the identified bead locations located within at least a portion of its respective tile. In an embodiment, the dark field reference constellation of a tile is the bead locations in an approximately 500 by 500 pixel area in the center of the tile. The dark field reference constellations may be determined at the time the dark field image is obtained for the two reference tiles (i.e., in step 704), or they may be identified in a separate imaging step.

At block 710, a florescent field image is obtained for each tile in the flow cell to be imaged. In an embodiment, a florescent field image is obtained by moving the flow cell 200 to the first nominal reference location associated with a first tile using an xy-stage 106 under control of the processor 120, illuminating the flow cell 200 with a filtered florescent field LED 112, and capturing light emitted by the DNA fragments with a camera 118. Subsequent tiles within the flow cell may then be imaged by iteratively moving the flow cell to the respective nominal reference location associated with each of those tiles, and repeating the capturing process.

At block 712, correction factors are determined and applied. The processor 120 may determine the correction factors and apply them to the expected bead locations from the dark field image to obtain corrected bead locations.

As the xy-stage moves the flow cell for imaging the individual tiles, error may be introduced by the physical movement from tile to tile. This error may be accommodated using software to compare a test region near the center of the fluorescent field image of each tile with the dark field image of the same tile to determine an offset, and incorporating the offset into a correction factor when reading out the intensity values at the bead locations. The test region may be a 500 by 500 pixel area at the center of the florescent field tile image. The process may be conducted by identifying a number of x, y bead locations determined in the dark field imaging step, and adding up the intensities of the same locations in the 500 by 500 pixel fluorescent field test region to obtain a total intensity value. Next, the 500 by 500 pixel test region is iteratively shifted by a predetermined amount, e.g., +/−10 pixels in the x and y directions, and the intensities at the x and y bead locations are once again measured and summed up for each iteration. Ultimately, the test region will be shifted to a point where the intensities of the fluorescent light emitted from the beads will overlie the x,y bead locations identified in the dark field imaging step, and the sum of the intensities will reach a peak value. At this point, the offset is determined as the total x and y shift distances necessary to obtain the peak intensity. These x and y values are used as a correction factor to shift the fluorescent field tile image data and thereby align the intensities across the entire fluorescent field image with the bead locations from the dark field image.

Additional correction factors may be determined. These other factors may include, for example, "pincushion" correction (correcting to account for a different diffraction angle of the particular wavelength as compared to the dark field LED), predetermined distortion corrections for known lens aberrations, and so on.

At block 714, the intensity values of the corrected fluorescent field image for the tile at the corrected bead locations are read out. The processor 120 may read out the intensity values at the corrected bead locations.

If florescent field images for other colors are to be determined, processing may return to block 710 with steps 710-714 repeated for each additional color. The flow cell is thereafter removed from the imaging station.

At block 716, the flow cell is repositioned for a second imaging session. A flow cell 200 on the chip 102 may be lifted by the transport 104 into position under an objective lens 108 of an imager 100 for imaging during the second imaging session.

At block 718, dark field constellations corresponding to the dark field reference constellations identified for the flow cell during the first imaging session (block 708) are determined. In an embodiment, the processor 120 identifies two dark field constellations corresponding to the dark field referenced constellations identified during the first imaging session—a first dark field constellation within the first tile and a second dark field constellation with a second tile. To do so, the xy-stage 106 moves the flow cell 200 to the nominal tile locations for each of the two tiles in which the constellations should be found and takes a dark field image of each. The dark field constellation within each tile may be the bead locations located within a 500 by 500 pixel area at the geometric center of the tile.

At block 720, offsets between the dark field constellations in the second imaging session and the dark field reference constellations in the first imaging session are determined. The offset between the constellations for a tile may be determined by iteratively shifting the dark field constellation in the second imaging session by a predetermined amount, e.g., +/−10 pixels in the x and y direction, and evaluating the intensities of this dark field image at the x,y locations corresponding to the bead locations found in the original reference constellation. The offset can be determined by summing the intensities of the dark field image at the expected x,y bead positions determined from the dark field reference constellation at each shift iteration, with the shift iteration producing the maximum intensity at the expected bead positions representing the offset. This may be essentially the same process as described above in step 712.

In one embodiment, a single dark field constellation is compared to a single reference constellation, and the offset between the two may be used to establish a linear offset of the flow cell in the x and/or y directions introduced when the flow cell was repositioned for a subsequent imaging. In embodiments using a second constellation as a second reference, the system can also calculate an angular offset that was introduced when the flow cell was repositioned for the subsequent imaging. For example, on each subsequent placement in the imaging station, the new location of the first constellation 402*a* may be determined and used as a first offset reference point, and the new location of the second constellation 402*b* may be determined and used as a second offset reference point. By comparing the first and second offset reference points to the original constellation locations, the total x,y offset and angular rotation of the flow cell are determined.

At block 722, new reference locations for the tiles are calculated to accommodate for any shift in the flow cell's position as compared to its position in the first round of imaging. In one embodiment, the processor 120 uses the x,y offset from one reference constellation to calculate a geometric correction factor for each of the nominal tile center locations that were used in step 704. For example, if the constellation found in step 718 was offset by +50 x pixels and +100 y pixels from the referenced constellation location, each nominal tile center location would be offset a corresponding −50 x and −100y pixels, and the xy-stage would be driven to these recalculated locations to place the center of each tile directly (or nearly directly) under the objective lens for further imaging steps.

In another embodiment, the processor 120 uses the x,y offset from two reference constellations to calculate a geometric correction factor for each of the nominal tile center locations that were used in step 704. In this case, the processor 120 may calculate x, y and angular correction factors for each nominal tile center location to accurately position the center of each tile under the objective lens 108. The shape of the flow cell remains constant between successive visits to the imaging system, and therefore the calculation of the geometric correction factors is a matter of basic geometry that need not be described herein. This process is expected to be more accurate than simply using an x,y offset as in the prior embodiment, but at the cost of greater processing time to evaluate a second constellation. As with the prior embodiment, the new reference locations are used to drive the xy-stage 106 to place the center of each tile directly (or nearly directly) under the objective lens 108 for the following steps.

At block 724, florescent field images are obtained for each tile during the subsequent imaging session. The florescent field images may be determined as described above with respect to block 710 using the reference locations as altered at block 722.

At block 726, correction factor(s) are applied to the fluorescent field image. The corrections factors applied in step 726 may include corrections as described above with reference to block 712 (e.g., registering the image to match the dark field image, pincushion and distortion correction, etc.). In addition, a correction factor also may be applied to rotate the fluorescent field image to correct for any angular offset identified in step 720. Following the corrections, the fluorescent field tile image should be properly shifted in the x,y direction and rotated to match the illuminated points and regions to the x,y locations of the beads determined from the original dark field imaging step for the respective tile.

At block 728, the intensity values at the corrected bead locations are read out. The processor 120 may read out the intensity values at the corrected bead locations.

If florescent field images for other colors are to be determined, processing may return to block 724 with steps 724-728 repeated for each additional color. The flow cell is thereafter removed from the imaging station. If the flow cell is to be imaged an additional time after further processing, processing may resume at block 716.

It will be appreciated from the foregoing example that embodiments of the invention can be used to help resolve a significant issue relating to sequencing by synthesis ("SBS") instruments that use multiple flow cells that are repeatedly mounted on and dismounted from an imaging system. By its nature, the SBS process requires repeated examination of exactly the same nucleotide strand to properly identify the nucleotides as they join the sequence. In conventional systems, fixed flow cells are used. Such systems have very little free play between the flow cell and the camera, so it is relatively easy to place the camera at almost exactly the same location during each successive imaging step. In contrast, in systems that use flow cells that are repeatedly dismounted and mounted on the imaging platform, there is much more free play. The free play in such devices may derive from clearances necessary to automate the mounting and dismounting process, manufacturing variances between one flow cell and the next, and so on. In these systems, it has been found that it is very difficult to properly align the flow cell in exactly the same location during successive visits to the imaging station. Since the beads being examined may be only a few hundred microns in diameter (or smaller), even a small amount of misalignment will make it impossible to correlate the data obtained from successive imaging steps, potentially rendering the device useless. The above process and versions thereof can be used to overcome this problem, and provide rapid image acquisition and processing in SBS instruments that use removable flow cells.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. An alignment method for use by an imager imaging deoxyribonucleic acid (DNA) fragments on a flow cell, the imager capturing intensity values at DNA fragment bead locations in tiles with each tile having a reference location in the flow cell, the method comprising:

during a first imaging session:
positioning the flow cell on an xy stage with the flow cell facing an imaging axis, the xy stage being movable along an x-axis and a y-axis, the x-axis being perpendicular to the y-axis, and the imaging axis being perpendicular to the x-axis and the y-axis,
illuminating the flow cell from the side of the flow cell with a first light to cause the first light to strike the DNA fragment beads from above the xy stage and at an angle relative to the imaging axis, and reflect off the DNA fragment bead locations,
operating the xy stage to reposition the flow cell to obtain a respective first image of each of a first tile and a second tile during a first imaging session, the respective first image comprising reflections of the first light, and
identifying a first reference constellation of bead locations within the first tile and a second reference constellation of bead locations within the second tile during the first imaging session; and during a second imaging session:
identifying a first pattern of light corresponding to the first reference constellation in the first tile, and a second pattern of light corresponding to the second reference constellation in the second tile,
determining a first offset between the first reference constellation during the first imaging session and the first pattern of light during the second imaging session,
determining a second offset between the second reference constellation during the first imaging session and the second pattern of light during the second imaging session,
moving the xy stage to alter the reference location of at least one tile during the second imaging session to correct for the first offset, and
applying at least one correction factor for reading out intensity values from the imager for the bead locations in the flow cell to correct for an angular offset determined from the first offset and the second offset.

2. The method of claim 1, where in the first offset comprises a linear offset of the flow cell between the first imaging session and the second imaging session.

3. The method of claim 1, further comprising:
obtaining a fluorescent field image for each tile of the flow cell during the second imaging session;
reading out the intensity values of the fluorescent field image at the bead locations identified in the first image as corrected by the applied at least one correction factor.

4. The method of claim 3, wherein the step of obtaining a fluorescent field image for each tile of the flow cell comprises:
positioning the flow cell for fluorescent imaging based on the altered reference location of the tile;
illuminating the tile with light of a first color;
capturing light emitted from the tile;
determining at least one additional correction factor by matching a portion of the emitted light to a corresponding portion in the first image;
applying the at least one additional correction factor for reading out intensity values;
wherein the intensity values are read out as corrected by the at least one correction factor and the at least one additional correction factor.

5. The method of claim 4, wherein the step of obtaining a fluorescent field image for each tile further comprises:
illuminating the tile with light of a second color;
capturing light emitted from the tile;
determining at least one additional correction factor by matching a portion of the emitted light to a corresponding portion in the first image;
applying the at least one additional correction factor for reading out intensity values;
wherein the intensity values associated with illuminating the tile with light of a second color are read out as corrected by the at least one correction factor and the at least one additional correction factor.

6. The method of claim 1, wherein the flow cell is imaged in 72 tiles including 3 rows with 24 tiles in each row, the first and second tiles are in the center row, and the second tile is at least 5 tiles away from the first tile.

7. The method of claim 6, wherein the second tile is at least 9 tiles away from the first tile.

8. The method of claim 1, further comprising:
removing the flow cell from the xy stage after the first imaging session; and
repositioning the flow cell on the xy stage during the second imaging session.

9. The method of claim 1, wherein the at least one correction factor comprises a difference between the first offset and the second offset.

10. The method of claim 8, further comprising:
obtaining a fluorescent field image for each tile of the flow cell during the second imaging session;
reading out the intensity values of the fluorescent field image at the bead locations identified in the first image as corrected by the applied at least one correction factor.

11. The method of claim 10, wherein the step of obtaining a fluorescent field image for each tile of the flow cell comprises:
positioning the flow cell for fluorescent imaging based on the altered reference location of the tile;
illuminating the tile with light of a first color;
capturing light emitted from the tile;
determining at least one additional correction factor by matching a portion of the emitted light to a corresponding portion of the first image;
applying the at least one additional correction factor for reading out intensity values;
wherein the intensity values are read out as corrected by the at least on correction factor and the at least one additional correction factor.

12. An imager for imaging deoxyribonucleic acid (DNA) fragments on a flow cell, the imager capturing intensity values at DNA fragment bead locations in tiles with each tile having a reference location in the flow cell, the imager comprising:
an xy stage supporting the flow cell with the flow cell facing an imaging axis, the xy stage being movable along an x-axis and a y-axis, the x-axis being perpendicular to the y-axis, and the imaging axis being perpendicular to the x-axis and the y-axis;
a dark field light emitting diode positioned along the y-axis to one side of the flow cell, the dark field light emitting diode being configured to illuminate the flow cell with a first light that strikes the flow cell from above the xy stage and a direction that is angled relative to the imaging axis;
a camera configured to capture images of flow cell tiles; and
a processor coupled to the xy stage and the camera, the processor configured to position the xy stage at a plurality of tile locations along the x-axis and the y-axis, and control the camera to:
reposition the xy stage to obtain a first image of each tile during a first imaging session, the first image comprising reflections from the first dark field LED;
identify a first reference constellation of bead locations within a first tile and a second reference constellation of bead locations within a second tile during the first imaging session;
identify, during a second imaging session, a first pattern of light corresponding to the first reference constellation and a second pattern of light corresponding to the second reference constellation;
determine a first offset between the first reference constellation during the first imaging session and the first pattern of light during the second imaging session;
determine a second offset between the second reference constellation during the first imaging session and the second pattern of light during the second imaging session;
alter the reference location of at least one tile during the second imaging session when positioning the xy stage to correct for the first offset; and
apply at least one correction factor for reading out intensity values from the camera for the bead locations in the flow cell to correct for an angular offset determined from the first offset and the second offset.

13. An alignment method for use by an imager imaging deoxyribonucleic acid (DNA) fragments in a flow cell, the method comprising:
providing a flow cell chip that extends in a horizontal plane having an imaging axis extending perpendicular thereto, the flow cell chip having a flow cell comprising a plurality of tiles, wherein each tile comprises a respective reference location and a respective plurality of DNA fragment beads;
positioning the flow cell chip on an xy stage, the xy stage being movable along an x-axis and a y-axis the x-axis being perpendicular to the y-axis and the imaging axis being perpendicular to the x-axis and the y-axis during a first imaging session:
   directing a first light from a side of the flow cell chip in relation to the imaging axis, such that the first light strikes the flow cell chip from above the xy stage and at an angle relative to the imaging axis, to thereby illuminate the flow cell chip from the side,
   positioning the flow cell chip with a reference location of a first tile at a predetermined position in relation to a camera, and obtaining an image of reflections along the imaging axis of the first light from DNA fragment beads in the first tile with each reflection indicating the position of a respective DNA fragment bead, and
   identifying a group of the reflections of the first light from the DNA fragment beads in the first tile as a first reference constellation;
after the first imaging session, repositioning the flow cell chip in relation to the camera;
during a second imaging session:
   attempting to position the flow cell chip with the reference location of the first tile at the predetermined position in relation to the camera, and
   examining DNA fragment bead locations in the first tile to determine the location of the first reference constellation; and
comparing the location of the first reference constellation during the second imaging session to the location of the first reference constellation during the first imaging session to determine a first offset between the position of the first tile in relation to the camera during the first imaging session and the position of the first tile in relation to the camera during the second imaging session.

14. The method of claim 13, wherein the first offset comprises at least one of a linear offset in the horizontal plane and an angular offset about the imaging axis.

15. The method of claim 13, wherein the respective reference location of each tile comprises a geometric center of each tile.

16. The method of claim 13, wherein the first reference constellation is located in a portion of the first tile surrounding a geometric center of the first tile.

17. The method of claim 13, wherein the first light comprises a red light emitting diode.

18. The method of claim 13, further comprising obtaining a fluorescent field image of at least one tile by:
activating a second light to cause the respective DNA fragment beads in the at least one tile to emit light at a wavelength that is different from a wavelength of the second light; and
obtaining an image of the light emitted from the respective DNA fragment beads in the at least one tile.

19. The method of claim 18, wherein the step of activating a second light is preceded by:
generating a modified respective reference location of at least one tile by subtracting the first offset from the respective reference location of the at least one tile; and
positioning the flow cell chip with the modified respective reference location of the at least one tile at the predetermined position in relation to the camera.

20. The method of claim 18, further comprising applying a correction factor to the fluorescent field image to remove a positional error caused by the first offset.

21. The method of claim 20, wherein applying the correction factor comprises determining intensity values of the fluorescent field image at respective intensity locations and applying a correction factor based on the first offset to shift the respective intensity locations to correspond to positions of respective DNA fragment beads identified during the first imaging step.

22. The method of claim 18, wherein:
activating a second light to cause the respective DNA fragment beads in the at least one tile to emit light at a wavelength that is different from a wavelength of the second light comprises positioning a mirror in an optical path from the at least one tile to the camera; and
activating a first light located to a side of the flow cell chip in relation to the imaging axis, to thereby illuminate the flow cell chip from the side comprises removing the mirror from the optical path from the at least one tile to the camera.

23. The method of claim 13, further comprising:
during the first imaging session:
   positioning the flow cell chip with a reference location of a second tile at the predetermined position in relation to the camera, and obtaining an image of reflections of the first light from DNA fragment beads in the second tile, and
   identifying a group of the reflections of the first light from the DNA fragment beads in the second tile as a second reference constellation;
during the second imaging session:
   attempting to position the flow cell chip with the reference location of the second tile at the predetermined position in relation to the camera, and
   examining DNA fragment bead locations in the second tile to determine the location of the second reference constellation; and
comparing the location of the second reference constellation during the second imaging session to the location of the second reference constellation during the first imaging session to determine a second offset between the position of the second tile in relation to the camera during the first imaging session and the position of the second tile in relation to the camera during the second imaging session.

24. The method of claim 23, wherein the first offset comprises a linear offset in the horizontal plane, and the second offset comprises an angular offset about the imaging axis.

25. The method of claim 24, further comprising:
generating a modified respective reference location of at least one tile by subtracting the first offset from the respective reference location of the at least one tile;
positioning the flow cell chip with the modified respective reference location of the at least one tile at the predetermined position in relation to the camera;
obtaining a fluorescent field image of the least one tile by:
   directing a second light to strike the flow cell chip along the imaging axis to cause the respective DNA fragment beads in the at least one tile to emit light at a wavelength that is different from a wavelength of the second light, and
   obtaining an image of the light emitted along the imaging axis from the respective DNA fragment beads in the at least one tile; and
applying a correction factor to the fluorescent field image to remove a positional error caused by the second offset.

26. The method of claim 23, wherein the first light illuminates the first tile and the second tile at the same angle of incidence.

27. The method of claim 13, wherein examining DNA fragment bead locations in the first tile to determine the location of the first reference constellation during the second imaging session comprises:
- directing the first light from the side of the flow cell chip in relation to the imaging axis, such that the first light strikes the flow cell chip from above the xy stage and at the angle relative to the imaging axis, to thereby illuminate the flow cell chip from the side;
- obtaining an image of reflections of the first light from DNA fragment beads in the first tile; and
- identifying the group of the reflections of the first light from the DNA fragment beads in the first tile as the first reference constellation.

28. The method of claim 13, wherein examining DNA fragment bead locations in the first tile to determine the location of the first reference constellation during the second imaging session comprises:
- directing a second light to cause the DNA fragment beads in the first tile to emit light at a wavelength that is different from a wavelength of the second light;
- obtaining an image of the light emitted along the imaging axis from the DNA fragment beads in the first tile; and
- identifying a portion of the light emitted from the DNA fragment beads in the first tile as the first reference constellation.

29. The method of claim 1, wherein the first light source comprises a dark field light emitting diode.

* * * * *